United States Patent [19]
Martin

[11] Patent Number: 5,704,937
[45] Date of Patent: Jan. 6, 1998

[54] OPERATIVE EQUIPMENT FOR FIXING SPINAL INSTRUMENTATION

[75] Inventor: Jean-Raymond Martin, Tornefeuille, France

[73] Assignee: Paulette Fairant, Tournefeuille, France

[21] Appl. No.: 605,036

[22] PCT Filed: Jul. 15, 1994

[86] PCT No.: PCT/FR94/00887
 § 371 Date: Feb. 27, 1996
 § 102(e) Date: Feb. 27, 1996

[87] PCT Pub. No.: WO95/05784
 PCT Pub. Date: Mar. 2, 1995

[30] Foreign Application Priority Data

Aug. 27, 1993 [FR] France ................... 93 10291
Feb. 7, 1994 [FR] France ................... 94 01440

[51] Int. Cl.$^6$ .................................... A61B 17/56
[52] U.S. Cl. .................... 606/61; 606/90; 606/102
[58] Field of Search .................... 606/53, 57, 90, 606/61, 102, 205, 206, 105

[56] References Cited

U.S. PATENT DOCUMENTS

| | | | |
|---|---|---|---|
| 3,486,505 | 12/1969 | Morrison | 606/90 |
| 3,865,105 | 2/1975 | Lode . | |
| 3,977,397 | 8/1976 | Kalnberz et al. . | |
| 4,066,082 | 1/1978 | Arcan et al. | 606/102 |
| 4,078,559 | 3/1978 | Nissinen . | |
| 4,271,836 | 6/1981 | Bacal et al. . | |
| 4,289,123 | 9/1981 | Dunn . | |
| 4,386,603 | 6/1983 | Mayfield . | |
| 4,445,513 | 5/1984 | Ulrich et al. . | |
| 4,448,191 | 5/1984 | Rodnyansky et al. . | |
| 4,611,582 | 9/1986 | Duff . | |
| 4,836,196 | 6/1989 | Park et al. . | |
| 4,854,496 | 8/1989 | Bugle . | |
| 4,898,161 | 2/1990 | Grundei | 606/90 |
| 4,946,458 | 8/1990 | Harms et al. . | |
| 4,964,400 | 10/1990 | Laico et al. | 606/90 |
| 5,122,130 | 6/1992 | Keller | 606/91 |
| 5,122,145 | 6/1992 | Fishbane | 606/102 |
| 5,219,349 | 6/1993 | Krag et al. . | |
| 5,281,223 | 1/1994 | Ray . | |

FOREIGN PATENT DOCUMENTS

| | | |
|---|---|---|
| 0140790 | 5/1985 | European Pat. Off. . |
| 0260044 | 3/1988 | European Pat. Off. . |
| 0418387 | 3/1991 | European Pat. Off. . |
| 0499037 | 8/1992 | European Pat. Off. . |
| 0470660 | 12/1992 | European Pat. Off. . |
| 1397395 | 3/1965 | France . |
| 2689750 | 10/1992 | France . |
| 2697744 | 5/1994 | France . |
| 2845647 | 8/1980 | Germany . |
| 3807346 | 6/1989 | Germany . |
| 848009 | 8/1979 | U.S.S.R. . |
| 888968 | 11/1979 | U.S.S.R. . |
| 780652 | 8/1957 | United Kingdom . |
| 2162065 | 1/1986 | United Kingdom . |
| 2198647 | 6/1988 | United Kingdom . |
| WO8504096 | 9/1985 | WIPO . |
| WO9002527 | 3/1990 | WIPO . |
| WO9213496 | 8/1992 | WIPO . |

*Primary Examiner*—Michael Buiz
*Assistant Examiner*—Julian W. Woo
*Attorney, Agent, or Firm*—Harold H. Dutton, Jr.

[57] ABSTRACT

An ancillary equipment for exerting and maintaining a force on a portion of the vertebral column for correcting and maintaining the shape and/or forces exerted on the vertebrae before and during a fixing operation of implanted rachidian instrumentation, comprising at least two active extremities (4, 5, 6) for cooperating respectively with two distinct vertebrae, comprising control rods for adjusting and maintaining the relative positions of the active extremities (4, 5, 6) in at least three orthogonal directions, by adjusting and maintaining the relative position of each active extremity (4, 5, 6) in at least one of said directions.

11 Claims, 4 Drawing Sheets

OPERATIVE EQUIPMENT FOR FIXING SPINAL INSTRUMENTATION

The invention concerns operative equipment for fixing implanted spinal instrumentation such as an osteosynthetic device, an intervertebral device for the treatment of instabilities or an implanted dynamic corrective orthosis, or other such.

BACKGROUND AND OBJECTS OF THE INVENTION

Spinal osteosynthetic devices are already known enabling scoliotic deformities to be treated, consisting of components for anchoring to the vertebrae, such as hooks or intrapedicular screws, and rods or frames fixed to the anchoring components to impose a relative position on the different vertebrae. These rigid or semi-rigid osteosynthetic devices rigidify the spinal column in the corrected position and are always associated with a bone graft and an arthrodesis of the vertebrae.

These known osteosynthetic devices still present many problems as regards the fitting and reliability of the anchoring components which withstand high stresses, taking into account the subsequent rigidity, during attachment of rods, plates or frames to the anchoring components which must be achieved simultaneously for reducing deformity.

Thus, the reduction of deformity when an osteosynthetic device is put into position still presents problems. In point of fact it must be possible to carry out this reduction in deformity at the same time as, and by the attachment of vertebral instrumentation, and this in three dimensions. In particular, with a scoliosis, it is advisable not only to replace the vertebrae in the same sagittal plane, but also to re-establish the kyphosis and/or lordosis while carrying out a deroration of the vertebrae. Osteosynthetic devices of the Cotrel-Dubousset type enable this problem to be partially resolved. They consist of two posterior bilateral rods, arched during the operation, immediately before their attachment to the anchoring components, in relation to the lateral deviation, then turned through 90° to place their curvature in a sagittal plane in order to re-establish the kyphosis or lordosis at least partially and to carry out a derotation of the vertebrae. The correction is limited by the fact that it is carried out only by the rod of the concavity which is first turned and then attached to the anchoring components. The rod placed in the convexity is modelled on the correction obtained and only has a stabilizing effect when inserted. The two rods are then connected to each other by transverse tensioning devices stabilizing the assembly in position. Nevertheless, the curvature of the rods determined essentially in relation to the lateral deviation to be corrected, does not necessarily correspond to an appropriate correction of the kyphosis or the lordosis. In addition, these devices are considered as among the most sophisticated and most rigid. The result is that their positioning remains difficult from the fact in particular of the instability of the hooks during corrective manoeuvres.

Apart from Cotrel-Dubousset devices, two other types of osteosynthetic devices are essentially used to treat deformities of the vertebral column. These consist on the one hand of Roy-Camille devices with plates and pedicular screws and their improvements, and on the other hand, of Luque or Dove devices with sub-lamina wires and their improvements. Roy-Camille devices are reserved for corrections with small amplitudes concerning a limited number of vertebrae, and do not permit effective derotation. Luque or Dove devices may cause serious neurological complications taking into account the passage of wires under the vertebral laminae in proximity to the spinal cord. All these devices do not provide a solution for the reduction of deformity which is any more satisfactory.

Intervertebral elastic devices are also known enabling degenerative lumbar instabilities to be treated. These devices generally consist of intervertebral ligaments or springs, sometimes accompanied by spacers interposed between the spinal processes or between intrapedicular screws. These ligaments or springs exert tensile forces tending to bring the vertebrae together and to reduce their relative mobility. In order to facilitate the fitting of these devices and to enable adjustments to be made more precisely, it would be desirable to be able to exert and measure the corrective forces before and during positioning of these devices, by a separate piece of equipment.

Moreover, it is also desired to have available operative equipment adapted to the fitting of new dynamic orthoses which preserve the natural physiological mobility of the vertebrae and comprise means of elastic return movement which need to be positioned extended and which need to have characteristics determined during fitting for the reduction of deformity and/or the forces to be corrected.

Known operative equipment consisting of single clamps with two articulated branches and exerting tensile or compressive forces, do not enable these various problems to be resolved in a satisfactory manner.

Bulky external equipment is also known for the reduction of scoliotic deformities consisting of a harness and/or a ring and/or belts associated with traction devices (motors, weights etc.) These pieces of equipment are not precise, not flexible in use, and do not enable large corrections of the positions of the vertebrae to be made precisely in three dimensions.

Thus, no known operative equipment permits precise control of the positions of the vertebrae in three dimensions in space in the frontal, sagittal and horizontal planes.

The object of the invention is thus to overcome these disadvantages and to offer operative equipment for correcting and/or maintaining with great precision and in three dimensions the shape and/or the forces exerted between the vertebrae before and during the fixing of implanted spinal instrumentation.

The object of the invention is also to provide operative equipment for fixing an implanted dynamic orthosis. In particular, the object of the invention is also to provide operative equipment which makes it possible to measure the movements and forces necessary to maintain the correction, and which will thus be incorporated in the installed osteosynthesis or dynamic orthosis instrumentation.

The object of the invention is also to provide operative equipment which is simple in its structure and use and takes up little room in the operating area.

DESCRIPTION OF THE INVENTION

In order to do this, the invention concerns operative equipment for exerting and maintaining constraints on a portion of the vertebral column with a view to correcting and/or maintaining the shape and/or the forces exerted on the vertebrae before and during the fixing of implanted spinal instrumentation, comprising at least two operational ends intended to cooperate respectively with two distinct vertebrae, wherein it comprises means for modifying and maintaining the relative positions of the operational ends in at least three orthogonal directions, by modifying and maintaining the relative position of each operational end in at least one of these directions.

According to the invention, the operative equipment comprises three operational ends intended to cooperate respectively with three distinct vertebrae. More particularly, the means for modifying and maintaining the relative positions of the operational ends compel the first two operational ends to move in translation in one direction, passing through these operational ends, which remains perpendicular to the same plane, and the third operational end interposed between the first two operational ends to move in the plane perpendicular to the plane passing through the first two operational ends.

According to the invention, the means for modifying and maintaining the relative positions of the three operational ends comprises means for varying the distance separating said first two operational ends and means for moving said third operational end in translation in two directions perpendicular to the direction passing through said first two operational ends.

According to the invention, said operational ends are operational ends of arms articulated to each other or to a common support. More particularly, and according to the invention, the operative equipment comprises at least three articulated arms each comprising an operational end and at least three control rods orthogonal in pairs associated with the articulated arms to modify and maintain the relative positions of their operational ends. According to the invention, each control rod comprises an axial stop cooperating with an arm, by means of a thread cooperating with an internal thread fixed to at least one other arm, or to one other control rod, or to an arm support, so that the distance of the arm cooperating with the stop can be modified in axial translation and maintained relative to the other arm or arms or to the other control rod or to the arm support. Each control rod of operative equipment according to the invention is provided with a manipulating handle making it possible in particular to operate it in rotation for modifying the relative positions of the corresponding operational ends.

In addition, and according to the invention, the operative equipment comprises dynamometric means for measuring the forces exerted on the operational ends to maintain their relative positions, and means for measuring movements of the operational ends during modifications to their relative positions.

The invention also concerns operative equipment comprising a combination of all or part of the characteristics referred to above or below.

DESCRIPTION OF THE DRAWINGS

Other characteristics and advantages of the invention will become apparent on reading the following detailed description which refers to the annexed drawings in which.

DETAILED DESCRIPTION OF THE PREFERRED EMBODIMENTS

In all the text, and unless stated to the contrary, the term "vertical" designates the axial direction of the spinal cord which does not correspond to the absolute vertical direction since the spinal cord has a curvature (kyphosis and lordosis). Similarly, the term "horizontal" designates any direction contained in the plane perpendicular to the vertical direction, the term "sagittal" designates any plane containing the antero-posterior vertical and horizontal directions, and the term "frontal" designates any plane containing the lateral vertical and horizontal directions. These terms are thus used with reference to each vertebra and not, in an absolute sense, in reference to the patient.

Figure 1:
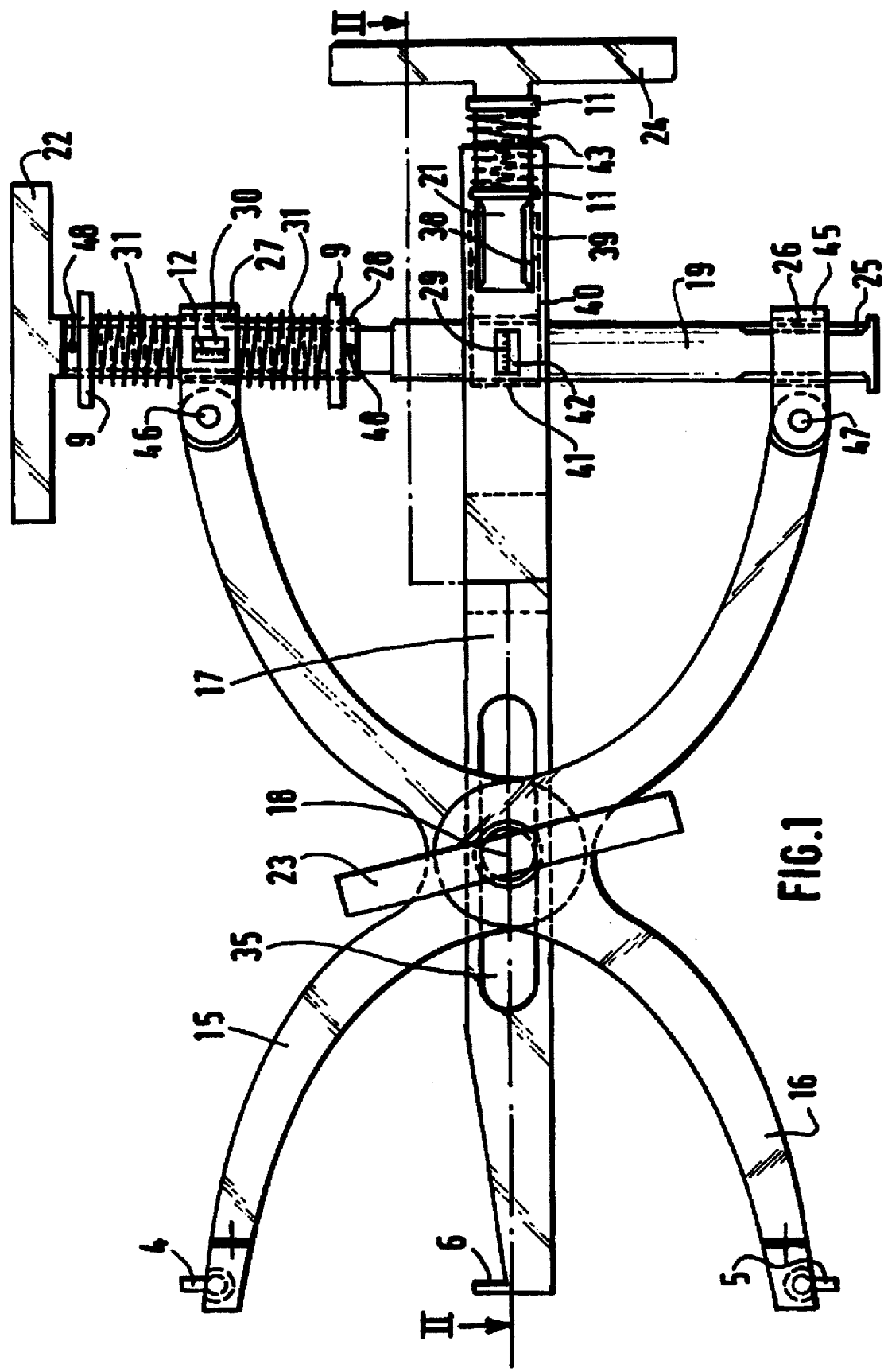
FIG. 1 is a diagrammatic rear view of an operative clamp according to the invention.
Figure 2:
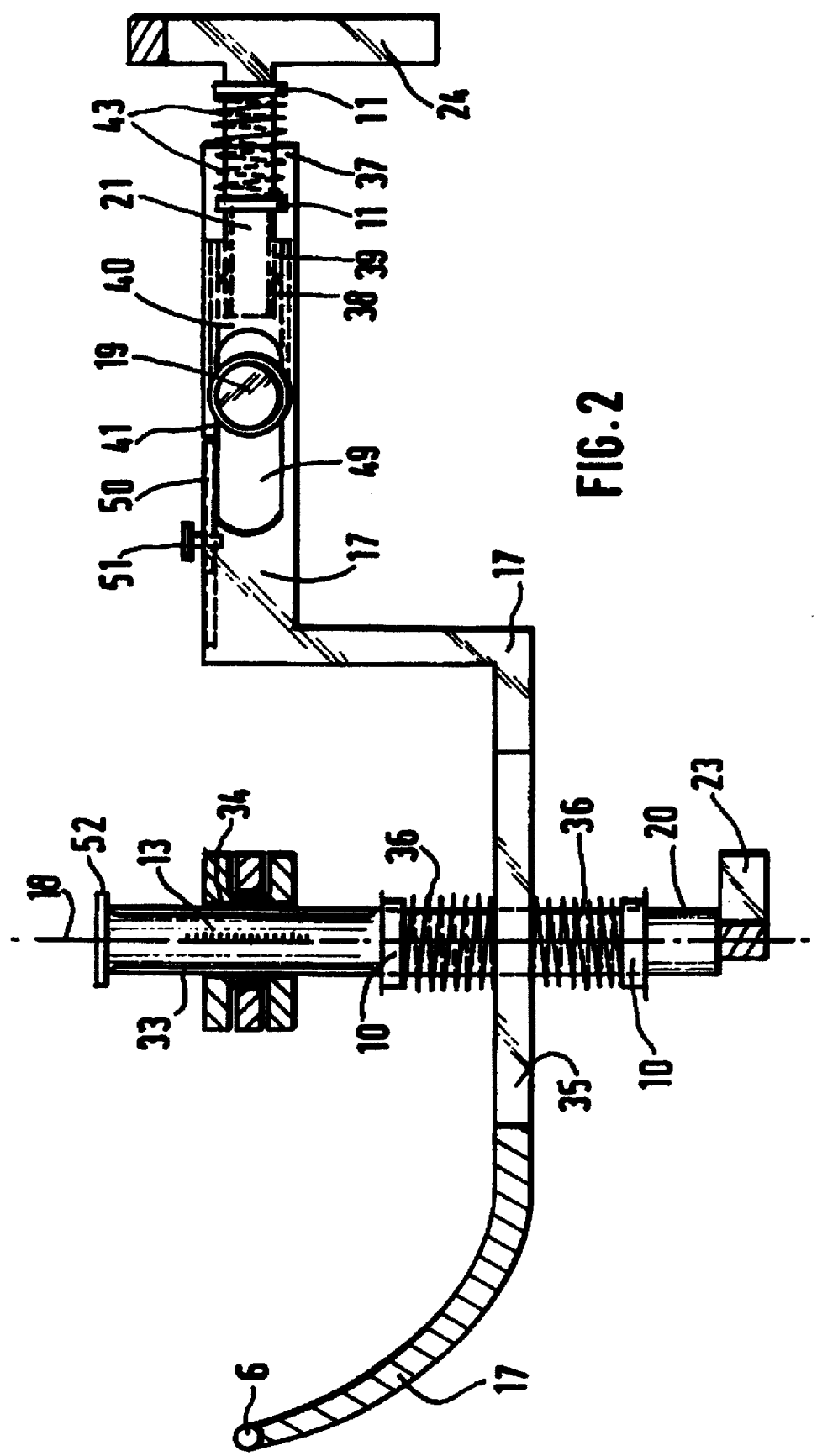
FIG. 2 is a diagrammatic view in section along the line II—II of FIG. 1.

FIGS. 1 and 2 represent an operative clamp according to the invention enabling in particular an implanted vertebral dynamic orthosis to be fixed. This clamp comprises three operational ends 4, 5, 6 intended to cooperate respectively with the anchoring components 1,2,3 of the orthosis on the vertebrae. Each of these operational ends 4, 5, 6 of the clamp is formed of a dog intended to be engaged in a drilling with a vertical axis provided near to the means of coupling the orthosis to the anchoring components 1, 2, 3. Each dog 4, 5, 6 which may be directed downwards or upwards (FIG. 1) can act in compression or in traction according to requirements. Thus, each anchoring element 1, 2, 3 comprises a drilling provided through a horizontal extension of the anchoring element which supports a coupling cylinder of a rod 8a, 8b of the orthosis. The drilling is preferably provided at the anterior and lateral side of the cylinder so as to make it possible to attach and detach the rod 8a, 8b while the clamp is associated with the anchoring components.

According to the invention, the clamp also comprises dynamometric means 9, 10, 11 for measuring the forces exerted on the end dogs 4, 5, 6 for maintaining their relative positions. The clamp also comprises means 12, 13, 29 for measuring the movement of the end dogs 4, 5, 6 during modifications to their relative position.

Each clamp consists of three articulated arms 15, 16, 17 bearing dogs 4, 5, 6 at their free end. In the following,the terms "upper" and "lower" are used with reference to FIG. 1. The clamp comprises an upper arm 15 bearing an upper end dog 4, a lower arm 16 bearing a lower end dog 5, and a middle arm 17 bearing a middle end dog 6 interposed between the upper dog 4 and the lower dog 5. These dogs 4, 5, 6, in particular the middle dog 6, may comprise a terminal screw in order to stabilize it on the corresponding anchoring component. The two upper and lower arms 15 and 16 are articulated to each other about a horizontal axis 18 at right angles to the direction passing through the two upper and lower dogs 4, 5. The arms 15, 16, 17 are articulated with respect to each other and controlled in their relative movements by three control rods 19, 20, 21 provided with manipulating handles 22, 23, 24.

A vertical control rod 19 comprises a thread 25 cooperating with an internal thread 26 of a sleeve-shaped extremity 45 of the lower arm 16 opposite the dog 5. The end 27 of the upper arm 15 opposite the dog 4 is in the form of a sleeve sliding around a cylinder 28 fixed to the vertical control rod 19, but whose position can be adjusted in translation in relation to the rod 19 by means of locking screws 48. This sleeve 27 is led captive between two compression springs 31 pressing at their opposite ends on dynamometric sensors 9 carried by the cylinder 28 and hence by the vertical control rod 19. The springs 31 and the sensors 9 thus form an axial stop in two directions for the extremity 27 of the upper arm 15 in relation to the control rod 19. The sleeve 27 also comprises a slot 30 enabling reading to be taken of a graduated scale 12 engraved on the cylinder 28 fixed to the rod 19. The end sleeves 45, 27 of the lower arm 16 and upper arm 15 cooperating with the vertical control rod 19 are articulated to these arms 16, 15 about an axis 47 and 46 respectively, parallel to the axis 18 of articulation between the arms 16, 15. When the handle 22 is turned, the end dogs 4, 5 are separated or brought together. If forces in the vertical direction do not bear on the dogs 4, 5, the upper sleeve 27 remains half way between the two sensors 9, the springs 31 not being activated. If on the contrary a force is needed to move the dogs 4, 5, one of the springs 31 is activated in compression to balance this force and to enable a change in position to be made. One of the dynamometric sensors 9 thus delivers an electric signal proportional to this force.

The middle arm 17 is articulated on the assembly thus formed by the upper and lower arms 15, 16. A sagittal control rod 20 extends along the axis 18 of articulation of the two upper and lower arms 15 and 16 in the sagittal direction. This rod 20 is provided, at its end, with a thread 33 engaged in an internal thread 34 of one of the arms 15, 16. The rod 20 also carries a graduated scale 13 enabling its position to be determined in relation to the arms 15,16. The end screw 52 of this rod 20 may be removed to disengage this rod 20 making it possible to demount the arm 17 if necessary. The middle arm 17 comprises an oblong slot 35 traversed by the control rod 20. This oblong slot 35 extends in a direction at right angles to the vertical direction passing through the upper and lower end dogs 4, 5, and to the horizontal axis of articulation 18 of the two upper and lower arms 15, 16. Thus movement is possible of the middle arm 17 in relation to the axis of articulation 18 and in this direction. The oblong slot 35 of the middle arm 17 is traversed by the sagittal control rod 20 which is held captive between the two springs 36, the opposite ends of which press on dynamometric sensors 10 carried by the rod 20. The springs 36 and the sensors 10 form an axial stop in two directions for the middle arm 17 in relation to the sagittal control rod 20. These dynamometric sensors 10 provide a measurement of the forces exerted on the dog 6 in the horizontal sagittal direction. By turning the handle 23, the position of the middle arm is thus modified, and hence of the middle dog 6 in the horizontal sagittal direction in relation to the frontal plane containing the upper and lower dogs 4, 5.

The end 37 of the middle arm 17 opposite the end dog 6 is associated with a frontal control rod 21 which enables the movements of this middle arm to be controlled in the horizontal frontal direction perpendicular to the vertical direction passing through the upper and lower end dogs 4, 5 and the axis of articulation 18 of the two upper and lower arms 15 and 16. This frontal control rod 21 comprises a threaded end 38 engaged in an internal thread 39 provided in a bearing 40 comprising a cylinder 41 surrounding the vertical control rod 19. The cylinder 41 carries a graduated scale 29 visible through a slot 42 of the middle arm 17. The end 37 of the middle arm 17 opposite the dog 6 slides about the frontal control rod 21 and is held captive between two springs 43, the opposite ends of which press on the dynamometric sensors 11 carried by the rod 21. The springs 43 and the sensors 11 thus form an axial stop in two directions for the end 37 of the middle arm 17 relative to the frontal control rod 21. Movement of the middle arm 17 in the horizontal frontal direction relative to the sagittal control rod 20 is permitted due to the oblong slot 35. The vertical control rod 19 passes through the middle arm 17 through an oblong slot 49 provided axially in this arm 17 to permit relative movements in the horizontal frontal direction. By turning the handle 24, the position of the middle dog 6 is modified in the frontal direction relative to the sagittal plane containing the upper and lower dogs 4, 5. One of the sensors 11 provides a measurement of the forces necessary for this movement. The arm 17 can be detached. To do this, the slot 49 is closed by a movable rear flap 50 locked by a screw 51. By withdrawing the flap 50, the rod 19 can be taken out of the slot 49. The frontal rod 21 and sagittal rod 20 are then completely unscrewed, which frees the arm 17.

Figure 3:
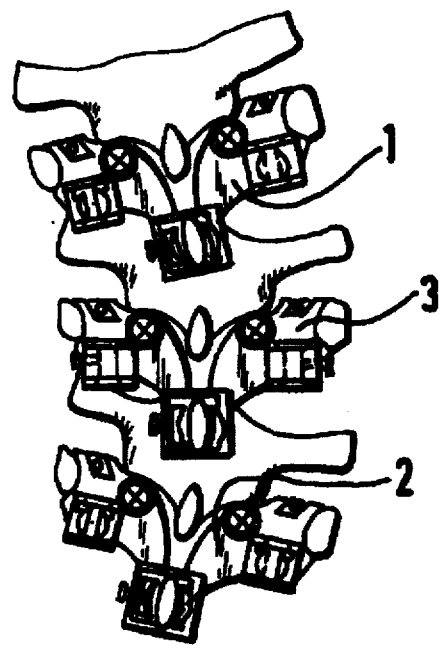
FIGS. 3 to 6 are diagrammatic views illustrating several successive stages in the fixing of an implanted dynamic orthosis with operative clamps according to the invention.
Figure 4:
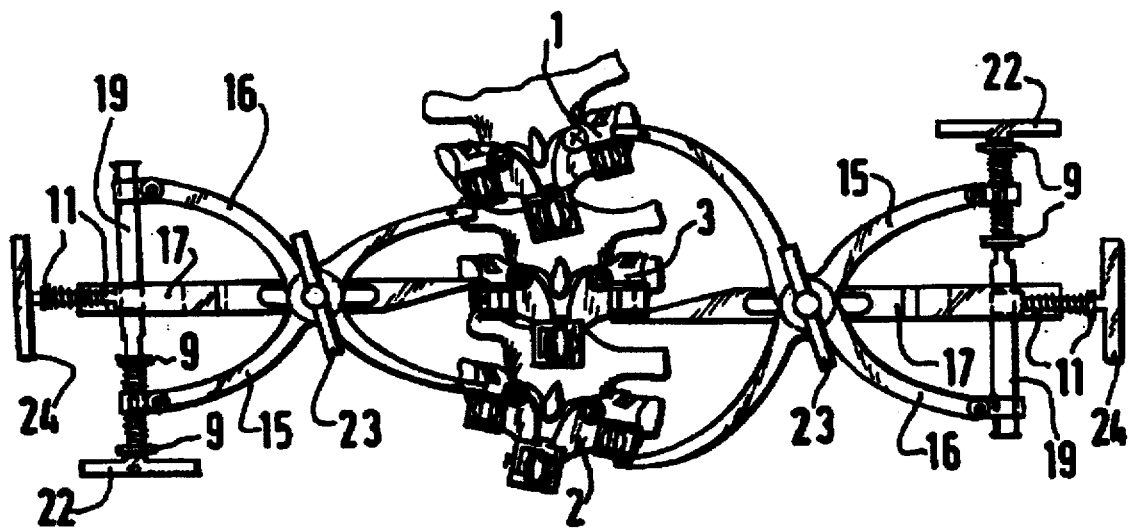
Figure 5:
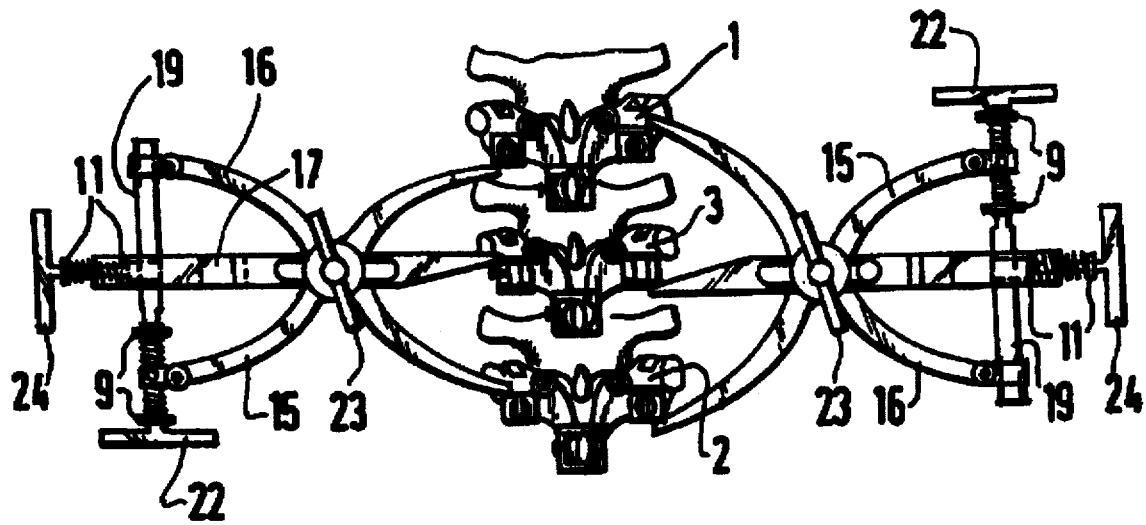
Figure 6:
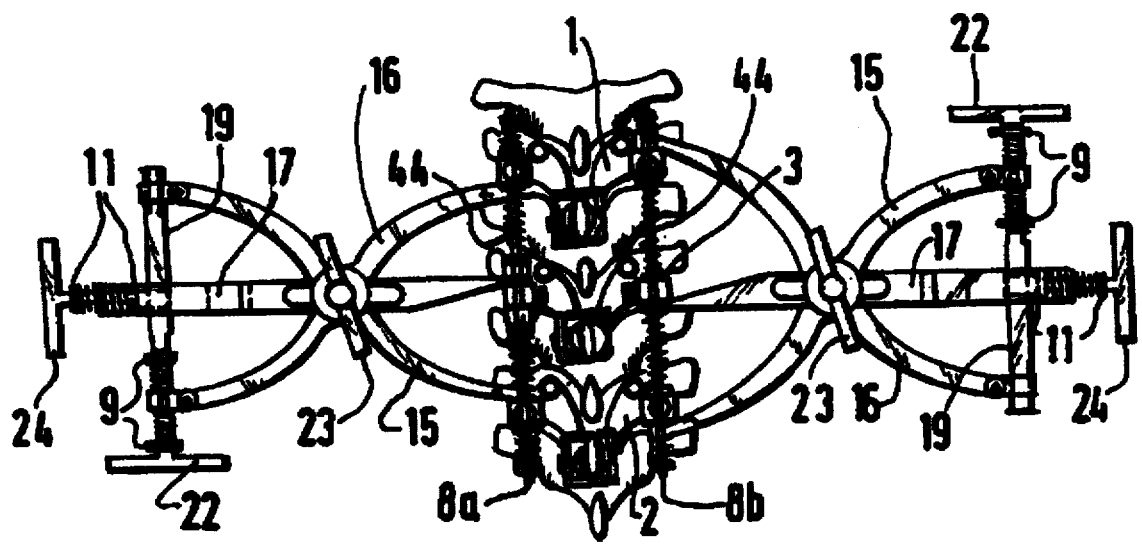

To attach an orthosis with operative equipment according to the invention, the vertebrae intended to receive the anchoring components 1, 2, 3 are uncovered, the anchoring components 1, 2, 3 are placed on and attached bilaterally to each vertebra concerned (FIG. 3), at least one operative clamp according to the invention is associated with the anchoring components 1, 2, 3 of each vertebra to be moved for the desired correction, and particularly a clamp for each rod 8a or 8b which must be fixed (FIG. 4), the handles 22, 23, 24 of each clamp are operated so as to place the vertebrae in a corrected position to reduce deformity and/or exert the desired forces (FIG. 5), the necessary maintenance forces applied to the anchoring components 1, 2, 3 of each vertebra are measured by means of the various dynamometric sensors 9, 10, 11 to maintain said corrected position, the characteristics are determined of the means of maintenance and the means of elastic return of the orthosis (rods 8a, 8b and springs 44) to produce elastic return forces similar to the measured maintenance forces, the means of maintenance and/or of elastic return are put in place (FIG. 6), namely the rods 8a, 8b and the springs 44 by associating them by the various means of coupling to the anchoring components 1, 2, 3, the operative corrective equipment is removed, and the surgical implantation operation is completed.

In FIGS. 3 to 6, the clamp placed to the right of the spinal apophyses is similar to that described and shown in FIGS. 1 and 2, and the clamp placed to the left is reversed, the upper arm 15 being associated with lower anchoring components 2 and the lower arm 16 being associated with the upper anchoring components 1. The dimensions and shape of the arms 15, 16 used, as well as the orientation of the end dogs 4 and 5 are chosen in relation to the distance between the corresponding vertebrae.

According to the invention, a deformity and/or forces are thus corrected by means of operative clamps entirely before associating the means of maintenance and/or elastic return (rods and springs), and this contrary to known osteosynthesis devices with which correction is carried out by or with components for rigidifying the vertebrae.

Maintenance forces are measured by dynamometric sensors 9, 10, 11 fixed to the operative equipment, namely along three orthogonal axes of translation of the end dogs 4, 5, 6, namely a vertical axis (vertical control rod 19), a sagittal axis (sagittal control rod 20), and a frontal axis (frontal control rod 21).

The various characteristics and dimensions of the means of maintenance and/or the means of elastic return of the orthosis are determined, at least in an approximate manner, by calculation with a data processing device programmed for this purpose from values of maintenance forces measured by the various dynamometric sensors. The desired efficiency of the means of maintenance or of elastic return of the orthosis are verified before removal of the clamps, by reading the cancellation of the static forces recorded by the dynamometers 9, 10, 11. The means of maintenance and of elastic return of the orthosis is then adjusted or changed completely or in part, according to requirements.

The operative clamps described above according to the invention thus make it possible to carry out a shape correction and/or to measure the forces exerted on the vertebrae before and during the fixing of the orthosis. When the clamps are associated with the anchoring components 1, 2, 3, they can be adjusted during the operation. It should also be noted that they allow the orthosis to be easily attached or detached (the rods 8a, 8b and the springs 44), and also characteristics of the orthosis to be adjusted until the maintenance forces supported by the clamps themselves are reduced to zero. When the operative clamps are removed, the dynamic orthosis thus itself exerts the forces necessary for correcting the shape and/or the forces necessary to maintain the portion of the vertebral column instrumented.

In the example shown, the operative clamps according to the invention enable five vertebrae to be instrumented by acting on three vertebrae of the corresponding portion of the vertebral column. Nevertheless, the shape and dimensions of the clamps may be adapted so that they can be associated with different lengths of vertebral column. In the case of a long curvature, five vertebrae for example may be instrumented by using a clamp with three arms on the three central vertebrae and on the two end vertebrae a clamp with two arms (the central arm of which will have been removed) which acts as a "bridge" over the first. Also, the operative clamps according to the invention can be used not only for correcting a scoliosis, but also for fixing any other spinal instrumentation, and particularly for treating congenital or acquired, cervical, dorsal or lumbar spinal deformity, or post-traumatic, tumoral, infectious, degenerative or other spinal instabilities. In particular, the operative clamps can make it possible to fix an orthosis or any other spinal instrumentation enabling vertebral articulations to be relieved for the treatment of a degenerate instability.

In the case where the operative clamps are used with equipment other than the dynamic orthosis shown, the ends of these clamps will be modified so that they will be adapted to the anchoring equipment concerned in order to achieve the desired vertebral correction before insertion of the connecting equipment which serves to maintain the position obtained.

Moreover, the operative equipment according to the invention can also be constructed not only in the form of a clamp, but also in the form of a frame or a support on which the arms are articulated while being able to slide. Also, the number of arms can be different from three, according to requirements.

I claim:

1. Operative equipment for exerting and maintaining constraints on a portion of the vertebral column for correcting and maintaining the shape and forces exerted on the vertebrae before and during fixing of an implanted spinal instrumentation, comprising:
    an upper arm having a first operational end for cooperating with a first vertebra,
    a lower arm having a second operational end for cooperating with a second vertebra,
    a middle arm having a third operational end for cooperating with a third vertebra, said arms being articulated to each other or to a common support for enabling modification of the relative positions of said operational ends along a vertical direction, a frontal horizontal direction and a sagittal horizontal direction by modification of the relative position of each of said operational ends along at least one of said vertical, frontal horizontal and sagittal horizontal directions,
    a vertical control rod provided with a manipulating handle, said vertical control rod extending along said vertical direction and being connected to said arms so as to enable the adjustment and maintenance of the relative position of at least one of said operational ends in said vertical direction,
    a sagittal control rod having a manipulating handle, said sagittal control rod extending along said sagittal horizontal direction and being connected to said arms so as to allow the adjustment and maintenance of the relative position of at least one of said operational ends in said sagittal horizontal direction,
    a frontal control rod provided with a manipulating handle, said frontal control rod extending along said frontal horizontal direction and being connected to said arms so as to allow the adjustment and maintenance of the relative position of at least one of said operational ends in said frontal horizontal direction, each of said control rods comprising:
        an axial stop cooperating with one of said arms, and
        at least one threaded portion cooperating with a threaded connection secured to at least one other of said arms or control rods for cooperating with said axial stop for axially adjusting and maintaining the relative position of said arms.

2. Operative equipment as in claim 1, wherein said third operational end is interposed between said first and second operational ends and moves in a plane perpendicular to said vertical direction passing through said first and second operational ends.

3. Operative equipment as in claim 1, wherein said vertical control rod is connected to said arms so as to allow the adjustment and maintenance of the distance between said first and second operational ends, and wherein said sagittal control rod and said frontal control rod are associated with said arms so as to allow the adjustment and maintenance of the relative translational position of said third operational end in two directions perpendicular to said vertical direction, and wherein said vertical direction passes through said first and second operational ends.

4. Operative equipment as in claim 1, wherein said upper and lower arms are articulated to each other about a horizontal axis of articulation perpendicular to an axis passing through said first and second operational ends, and wherein said vertical control rod cooperates with an end of said lower arm opposite said second operational end and with an end of said upper arm opposite said first operational end, for allowing adjustment and maintenance of the relative position of said first and second operational ends in said vertical direction.

5. Operative equipment as in claim 4, wherein said sagittal control rod extends along said horizontal axis of articulation and includes a threaded connection with one of said upper and lower arms, and comprises at least one axial stop cooperating with said middle arm for allowing adjustment and maintenance of the relative position of said third operational end in said sagittal horizontal direction.

6. Operative equipment as in claim 5, wherein said frontal control rod includes a threaded connection with said vertical control rod, and at least one axial stop cooperating with said middle arm for allowing adjustment and maintenance of the relative position of said third operational end in said frontal horizontal direction.

7. Operative equipment as in claim 6, wherein said middle arm includes an elongated slot extending perpendicular to said vertical direction and to said axis of articulation, said sagittal control rod passing through said elongated slot.

8. Operative equipment as in claim 6, wherein said middle arm includes an oblong slot, said vertical control rod passing through said oblong slot for enabling relative movement in said frontal horizontal direction.

9. Operative equipment as in claim 1, and including dynamometric means for measuring the forces exerted on said operational ends for maintaining their relative positions.

10. Operative equipment as in claim 1, wherein said arm cooperating with said axial stop is held between two springs, the opposite ends of said springs bearing on dynamometric sensors carried by said control rod.

11. Operative equipment as in claim 1, and including means for measuring the movements of said operational ends during adjustment of their relative positions.

* * * * *